United States Patent
Paufique (10) Patent No.: US 11,839,680 B2
(45) Date of Patent: *Dec. 12, 2023

(54) TENSING AND/OR FILM-FORMING COSMETIC AGENT CONSISTING OF GALACTOMANNANS AND CROSS-LINKED SULPHATED GALACTANS

(71) Applicant: Societe Industrielle Limousine D'Application Biologique, Objat (FR)

(72) Inventor: Jean Paufique, Objat (FR)

(73) Assignee: SOCIETE INDUSTRIELLE LIMOUSINE D'APPLICATION BIOLOGIQUE, Objat (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/072,593

(22) PCT Filed: Jan. 27, 2017

(86) PCT No.: PCT/EP2017/051849
§ 371 (c)(1),
(2) Date: Jul. 25, 2018

(87) PCT Pub. No.: WO2017/129792
PCT Pub. Date: Aug. 3, 2017

(65) Prior Publication Data
US 2019/0038543 A1 Feb. 7, 2019

(30) Foreign Application Priority Data
Jan. 29, 2016 (FR) ...................................... 1650736

(51) Int. Cl.
| | |
|---|---|
| *A61K 8/73* | (2006.01) |
| *A61Q 17/00* | (2006.01) |
| *A61K 8/02* | (2006.01) |
| *A61Q 19/08* | (2006.01) |
| *A61K 36/04* | (2006.01) |
| *A61K 36/48* | (2006.01) |
| *A61K 36/482* | (2006.01) |
| *A61K 36/489* | (2006.01) |
| *A61K 8/9717* | (2017.01) |
| *A61K 8/9789* | (2017.01) |

(52) U.S. Cl.
CPC ............ *A61K 8/737* (2013.01); *A61K 8/0204* (2013.01); *A61K 8/73* (2013.01); *A61K 8/9717* (2017.08); *A61K 8/9789* (2017.08); *A61K 36/04* (2013.01); *A61K 36/48* (2013.01); *A61K 36/482* (2013.01); *A61K 36/489* (2013.01); *A61Q 17/00* (2013.01); *A61Q 19/08* (2013.01); *A61K 2800/5922* (2013.01); *A61K 2800/95* (2013.01)

(58) Field of Classification Search
CPC ............ A61K 8/737; A61K 2800/5922; A61K 2800/95; A61K 36/04; A61K 36/48; A61K 36/482; A61K 36/489; A61K 8/0204; A61K 8/73; A61K 8/9717; A61K 8/9789; A61Q 17/00; A61Q 19/08
See application file for complete search history.

(56) References Cited

U.S. PATENT DOCUMENTS

| | | | | |
|---|---|---|---|---|
| 4,661,475 | A * | 4/1987 | Bayerlein | ................ A61K 8/73 514/54 |
| 5,093,485 | A * | 3/1992 | Svensson | ................ B05D 5/00 428/411.1 |
| 7,189,846 | B2 * | 3/2007 | Learmonth | .......... C07D 223/28 540/589 |
| 9,463,149 | B2 | 10/2016 | Paufique | |
| 2002/0076769 | A1 | 6/2002 | Brady et al. | |
| 2005/0118130 | A1 | 6/2005 | Utz et al. | |
| 2005/0208160 | A1 | 9/2005 | Paufique | |
| 2006/0099167 | A1 * | 5/2006 | Staudigel | ................ A61K 8/463 424/70.13 |
| 2011/0256087 | A1 * | 10/2011 | Fabre | ...................... A61Q 5/06 424/74 |

FOREIGN PATENT DOCUMENTS

| | | |
|---|---|---|
| EP | 0730867 A2 | 9/1996 |
| FR | 2881349 A1 | 8/2006 |
| FR | 1944065 A1 | 7/2008 |
| FR | 3018448 A1 | 9/2015 |
| JP | 10-036403 * | 2/1998 |

OTHER PUBLICATIONS

Necas, J. et al., Carrageenan: a review, Veterinarni Medicinia, 58, 2013 (4): pp. 187-205 (Year: 2013).*
Nguyen, Bach T, et al., Carbohydrate polymers 112 (2014), pp. 10-15 (Year: 2014).*
Guiry, et al., "Kappaphycus Alvarezii (Doty) Doty ex P.C.Silva", AlgaeBase, Feb. 26, 2013, pp. 1-4.
Aboratorium Kosmetyczne Floslek, "Dermal Filler Day Cream SPF 15", Feb. 5, 2014, pp. 1-4, XP002759145.
(Continued)

*Primary Examiner* — Andrew S Rosenthal
*Assistant Examiner* — Lyndsey M Beckhardt
(74) *Attorney, Agent, or Firm* — Greer, Burns & Crain, Ltd.

(57) ABSTRACT

A cosmetic or dermocosmetic agent consisting of: galactomannans having molecular weights between 5 and 630 kDa, and crosslinked sulfated galactans having molecular weights between 7 and 3000 kDa. Methods of using the agent, including for skin tensing and rejuvenation.

16 Claims, 2 Drawing Sheets

(56) References Cited

OTHER PUBLICATIONS

Telosomyl, "Protecting Telomeres to Ensure Longevity" Silab, Apr. 1, 2012, pp. 1-2.
Parker et al., "Binding of galactomannans to kappa-carrageenan after cold mixing", Carbohydrate Research, Jul. 21, 1995, pp. 91-86, vol. 272, No. 1.
Fernandes et al., "A Rheological Characterization of Kappa-Carrageenan/Galactomannan Mixed Gels: A Comparison of Locust Bean Gum Samples", Carbohydrate Polymers, Applied Science Publishers, Ltd., Jan. 1, 1991, pp. 253-274, vol. 16, No. 3.
XP-002759680, Biosis / Biosis, Aug. 23, 2016, 1 page.
XP-002759681, Biosis / Biosis, Aug. 23, 2016, 1 page.
XP-002759682, Biosis / Biosis, Aug. 23, 2016, 1 page.

* cited by examiner

Abscissa scale: between 0, 5, 10, 15, 20, 25, 30, 35 mU
Ordinate scale: between 0, 2000, 4000, 6000, 8000, 10,000, 12,000, 14,000, 16,000 nRU

Figure 1

Efficacy ++++

Figure 2A

Efficacy +++

Figure 2B

Efficacy ++

Figure 2C

Efficacy +

Figure 2D

Efficacy -

Figure 2E

TENSING AND/OR FILM-FORMING COSMETIC AGENT CONSISTING OF GALACTOMANNANS AND CROSS-LINKED SULPHATED GALACTANS

CROSS-REFERENCE TO RELATED APPLICATIONS

This application is a 371 US national stage application of PCT/EP2017/051849 filed Jan. 27, 2017 which claims a benefit of priority from French patent application FR1650736 filed Jan. 29, 2016, the entire disclosures of both applications are herein incorporated by reference.

TECHNICAL FIELD OF THE INVENTION

The present invention relates to particular cosmetic agents having a tensing and/or film-forming effect and to their use for cosmetic or dermocosmetic applications.

BACKGROUND

Women are perpetually seeking solutions for keeping their skin young and in good health. They are looking for the product that can erase the signs of time and allow them to protect themselves from the harmful effects of an ever-more aggressive environment. Indeed, as a result of industrialization and the increasing size of cities, individuals are regularly exposed to allergens, irritating molecules and fine particles. The latter are emitted in particular by vehicles and have devastating effects on health. In addition to their impact on the respiratory system, they result in major damage to the skin by accelerating its aging: appearance of wrinkles and pigmented spots, flabby skin, loss of elasticity and lack of radiance.

Confronted with this problem, the cosmetics market proposes an extensive line of anti-aging and protective care products. There are products that aim to remodel the skin at depth and long-term in order to restore its youthfulness. In addition, a variety of antioxidants, detoxifying agents and stimulants of natural defenses is available to help the skin protect itself.

However, in addition to these "long-term" treatments, consumers also wish to have immediate results. Thus, henceforth and very commonly, care will incorporate lifting agents capable of instantaneously improving the signs of aging. Since 2010, there has been progress in skin care with a new category of active substances: the "second-skin" active substances. These substances, having a short-term action, are incorporated for their radiance conferring action and their protective action against external aggression.

SUMMARY

The aim of the present invention is to propose novel cosmetic agents having a perceptible tensing effect and a protective "second skin" film and lifting effect capable of boosting skin youthfulness.

For this purpose, the invention relates to cosmetic or dermocosmetic agents consisting of the combination of specific biopolymers, namely galactomannans of selected molecular weight and crosslinked sulfated galactans of selected molecular weight.

In particular, the invention relates to a cosmetic or dermocosmetic agent consisting of:
galactomannans having molecular weights between 5 and 630 kDa, and
crosslinked sulfated galactans having molecular weights between 7 and 3000 kDa. Preferably, the invention relates to a cosmetic or dermocosmetic agent consisting of:
galactomannans having an average molecular weight between 5 and 120 kDa, and
crosslinked sulfated galactans having an average molecular weight between 7 and 1100 kDa.

Even more preferably, the invention relates to a cosmetic or dermocosmetic agent consisting of:
galactomannans having an average molecular weight between 8 and 80 kDa, and
crosslinked sulfated galactans having an average molecular weight between 8 and 200 kDa.

These biopolymers have powerful biomechanical and film-forming properties which confer a protective second-skin efficacy. Advantageously, they are produced without using chemical agents and meet the ecodesign requirements. With these particular biopolymers, the skin is protected and recovers radiance and attractiveness. The signs of aging are instantaneously erased.

The invention thus also relates to the cosmetic use of this cosmetic agent.

The invention further relates to the cosmetic compositions which include the cosmetic agent according to the invention and to a method for cosmetic treatment of the skin using these compositions.

Other features and advantages will become apparent in the detailed description of the invention given below in reference to the appended figures.

DEFINITIONS

The term "cosmetic or dermocosmetic agent" or "agent" in the sense of the invention is understood to mean an ingredient, an active substance or an excipient suitable for use in a cosmetic or dermocosmetic composition. The agent according to the invention consists of biopolymers and can also be referred to by the term "biopolymer" in the present application.

In the sense of the invention, "biopolymers" are understood to mean polymers originating from plant raw materials, as opposed to synthetic polymers which are obtained by chemical synthesis.

"Film-forming effect" is understood to mean an effect which can create a film which is not visible to the naked eye on the surface of the skin and thus protect the skin from external aggression such as pollution and allergens.

"Tensing effect" is understood to mean a tensing effect on the skin and, as a result of this tensing effect, a smoothing of the skin and an immediate reduction of the wrinkles and small wrinkles.

In the sense of the invention, "film-forming" is understood to mean a biopolymer which has a film-forming effect, that is to say any biopolymer which is soluble in water at the concentration of 7% by weight or at the maximum concentration at which it forms a medium of homogeneous appearance, and which, once it has been dried for 24 h at 40° C., produces a film which requires a weight of at least 100 g to be broken in the test described in the present application.

"Tensing agent," in the sense of the invention, is understood to mean a biopolymer which has a tensing effect, that is to say any biopolymer which is soluble in water at the maximum concentration of 7% by weight or at the maximum concentration at which it forms a medium of homogeneous appearance and which, at this concentration, produces a retraction scored as at least "+++" in the test described in the present application.

"Average molecular weight" of a mixture of molecules in the sense of the invention is understood to mean the average of the molecular weights by weight of each molecule of the mixture.

"Mixture of homogeneous appearance" is understood to mean a medium that has no aggregates visible to the naked eye.

"Crosslinked" in the sense of the invention is understood to mean a biopolymer in which a three-dimensional network was formed by means of the formation of chemical or physical bonds between the molecules of the biopolymer.

DETAILED DESCRIPTION OF THE INVENTION

The invention thus relates to a cosmetic or dermocosmetic agent consisting of:
galactomannans having molecular weights between 5 and 630 kDa, and
crosslinked sulfated galactans having molecular weights between 7 and 3000 kDa. Preferably, the invention relates to a cosmetic or dermocosmetic agent consisting of:
galactomannans having an average molecular weight between 5 and 120 kDa, and
crosslinked sulfated galactans having an average molecular weight between 7 and 1100 kDa.

These are thus selected particular biopolymers having selected specific sizes.

Preferably:
the galactomannans have an average molecular weight between 8 and 80 kDa,
the crosslinked sulfated galactans have an average molecular weight between 8 and 200 kDa.

Figure 1:
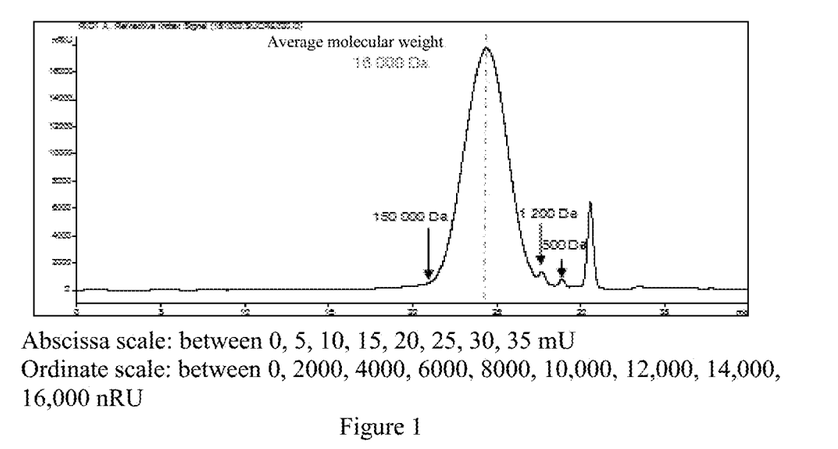
FIG. 1 represents a chromatogram of an example of an agent according to the invention.
Figure 2A:
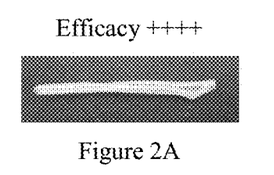
FIGS. 2A, 2B, 2C, 2D and 2E represent the scale from "−" (FIG. 2E), "+" (FIG. 2D), "++" (FIG. 2C), "+++" (FIG. 2B) to "++++" (FIG. 2A) for evaluating the force of retraction of an agent according to the invention.
Figure 2B:
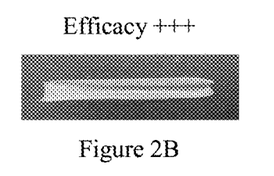
Figure 2C:
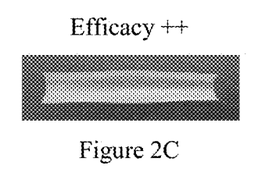
Figure 2D:
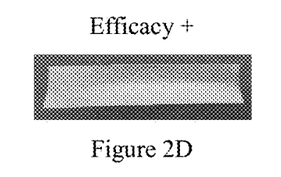
Figure 2E:
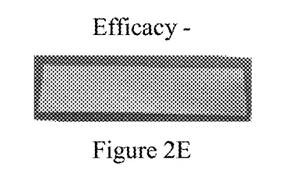

The determination of the molecular weights of these biopolymers of saccharide nature is preferably carried out by steric exclusion chromatography. This liquid chromatography method makes it possible to separate the macromolecules as a function of their hydrodynamic volume (steric exclusion chromatography). The solutes are eluted in order of decreasing molecular weights after passage through 3 series-mounted gel permeation columns (PL aquagel-OH C60, C40 and C30 columns). The compounds are detected by means of a refractive index detector. The molecular weights of the carbohydrates are evaluated by comparison of the retention times of the peaks detected in the agents according to the invention with the retention times of standards. The average molecular weight of an agent corresponds to the average of the molecular weights weighted by the intensity of each one. For example, the agent whose chromatogram is represented in FIG. 1 contains biopolymers having molecular weights between 1.2 and 150 kDa and an average molecular weight of 16 kDa.

Physically, the biopolymers according to the invention preferably have a low viscosity. The viscosity is measured at ambient temperature with the aid of a Brookfield viscosimeter model DV-I+. The Brookfield viscosimeter determines the viscosity of a fluid from the deformation exerted on a spring, generated by the rotation of a disk in this fluid. A product is considered to be viscous if the viscosity exceeds 1000 centipoise.

In addition, these biopolymers can be defined as having a tensing effect. This tensing effect can be defined by the characterization of the retraction force on a synthetic skin model or by a sensory study using a panel of sensory experts.

The retraction force of the polymer can be characterized by an in vitro test. This model is known to the person skilled in the art and has been described in the patent application EP1944065.

The test is carried out on a homogeneous solution of biopolymers diluted in water at a concentration of 7% by weight. The homogeneous mixture is deposited in the form of a film on a synthetic skin having a thickness of approximately 100 μm and an initial width of 10 mm. After drying at 22±3° C. and 40±10% relative humidity, the synthetic skin has a retracted width due to the tension exerted by the deposited polymer.

This retraction is evaluated visually and quantified on a scale from "−" to "++++" which is represented in FIGS. 2A to 2E.

A product is considered to be a tensing agent based on this test, if the retraction is scored as at least "+++."

The tensing effect can also be evaluated by a sensory study carried out using a panel of sensory experts. The study can be carried out by formulating the agents to be tested in the form of a gel.

The gel was produced using the following formula:
agent according to the invention: 0.50%
preservative: 0.23%
carbomer (Ultrez 10, Noveon): 0.27%
Water: sufficient quantity for 100%
(The Percentages are by Weight).

Each expert scores the intensity of the sensation perceived after the application of the product (agent according to the invention or placebo) on crow's feet wrinkles on a scale from 0 to 10 (0: no tensing effect perceived, 10: considerable tensing effect). The scoring is carried out 3 minutes, 5 minutes and 10 minutes after the application of the product.

The average of the scores obtained at each time is calculated for each expert.

A product is considered to be a tensing agent if the average of the scores obtained is greater than 3.

Finally, the film-forming effect of the agents according to the invention can be characterized by means of a texturometer. The principle consists in quantifying the film-forming effect of the samples to be tested by applying a pressure on them until the film breaks.

The samples are prepared as follows:
Drying of the solutions containing the agents according to the invention at 7% (w/w) for 24 h at 40° C.,
Obtention of films having a thickness between 30 and 40 μm.

The samples to be tested are deposited on the surface of a flexible and deformable foam, which makes it possible to impose considerable deformation on the film of biopolymers. The substrate consists of a urethane elastomer foam having a thickness of 5 mm; it mimics the surface and the elasticity of the skin.

The study can be carried out with a TA-XTplus Texturometer from the company Stable Micro System.

A cylindrical punch exerts mechanical stress on the sample at a constant speed of displacement.

A curve of the weight exerted (g) as a function of the time (sec) is obtained, from which it is possible to determine the weight necessary to break the film.

The necessary weight for breaking the samples depends on the viscoelastic properties of each sample. A product is considered to be film-forming if the weight exerted to break the film of the product is greater than 100 g.

The cosmetic or dermocosmetic agent according to the invention thus contains galactomannans having an average molecular weight between 5 and 120 kDa, preferably between 8 and 80 kDa.

The galactomannans are known as emulsifiers, thickeners commonly used in cosmetics and the food sector. They are polysaccharides of very large size (approximately 3000 kDa).

The viscosity of these polysaccharides is proportional to the size of the polysaccharides and is responsible for the thickening effect.

The biopolymers of the invention consist of galactomannans, preferably selected based on their average molecular weight between 5 and 120 kDa, that is to say that they are obtained preferably by transformation of native galactomannans (of very large size) in particular by hydrolysis.

They can be obtained in particular from galactomannans of tara (*Caesalpinia spinosa*), guar (*Cyamopsis tetragonoloba*), carob tree (*Ceratonia siliqua*), but also of senna (*Cassia angustifolia*), golden rain tree (*Cassia fistula*), cassia (*Cassia obtusifolia* or *Cassia tora*), Chinese carob (*Gleditsia sinensis*), honey locust (*Gleditsia triacanthos*), Japanese pagoda tree (*Sophora japonica*) and/or fenugreek (*Trigonella foenum-graecum*).

The particular selected galactomannans according to the invention are produced as follows:
Solubilization of the powder of native galactomannans in water at a concentration of at least 20 g/L,
Controlled hydrolysis by chemical or enzymatic route; the size of the biopolymers according to the invention is inversely proportional to the duration of the hydrolysis, or to the concentration of enzyme or chemical agent used.
Separation of the soluble phase and the insoluble phase, in order to eliminate the insoluble phase,
Selection by membrane filtration(s) of the galactomannans having an average molecular weight between 5 kDa and 120 kDa.

A low-viscosity liquid product A containing selected galactomannans having an average molecular weight between 5 kDa and 120 kDa is obtained. These selected galactomannans preferably have an average molecular weight between 8 and 80 kDa.

The size of the galactomannans selected is determined by steric exclusion chromatography.

The tensing effect is evaluated on a retraction model using synthetic skin or by a panel of sensory experts.

The viscosity is determined by a viscosimeter.

The force causing the rupture of the film produced with the active ingredients is evaluated by a texturometer and expressed in weight.

The characteristic results of several examples of agents according to the invention consisting of galactomannans having an average molecular weight between 5 and 120 kDa on the one hand, and of galactomannans having an average molecular weight outside of said range to which the invention relates are presented in Table 1 below:

TABLE 1

| Minimum and maximum molecular weights | Average molecular weight | Viscosity (cP) or physical state | Tensing effect on retraction model | Sensory tensing effect | Weight resulting in the breaking of the film (g) |
|---|---|---|---|---|---|
| | 3 kDa from CeS | 3.4 | − | NT** | NT** |
| | 4.7 kDa from CaS | Liquid | − | | |
| 0.5 to 40 kDa | 5.4 kDa from CaS | 70 | + | NT** | NT** |
| | 7.2 kDa from CaS | liquid | + | | |
| 0.7 to 62 kDa | 9.5 kDa from CaS | liquid | ++ | | |
| | 10 kDa from CaS | 85 | +++ | NT** | NT** |
| 0.9 to 117 kDa | 13.5 kDa from CaS | liquid | +++ | | |
| | 18 kDa from CaS | 90 | +++ | 4.5 | 280 |
| | 18.9 kDa from CeS | 184 | +++ | | |
| 1.2 to 171 kDa | 19 kDa from CaS | liquid | +++ | | |
| 1.5 to 215 kDa | 22 kDa from CaS | liquid | +++ | | |
| 1.6 to 160 kDa | 25 kDa from CaS | liquid | +++ | | |
| | 63 kDa from CyT | 140 | +++ | 4.4 | 410 |
| | 80 kDa from CyT | | +++ | | |
| | 117 kDa from CyT | NM* | ++ | NT** | NT** |
| | 125-130 kDa from CyT | | + | | |
| | 150 kDa from CyT | NM* | + | NT** | NT** |
| | 180 kDa from CyT | NM* | − | NT** | NT** |
| Non-hydrolyzed CaS gum | 1980 kDa from CaS | >3125 | − | NT** | NT** |

NM*: not measured;
NT**: not tested
CaS: *Caesalpinia spinosa*
CeS: *Ceratonia siliqua*
CyT: *Cyamopsis tetragonoloba*

These results clearly show that the galactomannans of high average molecular weight (>120 kDa) and the galactomannans of low average molecular weight (<5 kDa) do not exhibit the desired tensing effect on the retraction model.

The tensing effect visualized on the model of retraction using synthetic skin correlates with the evaluation of the tensing effect perceived by a panel of sensory experts. This confirms that the selected galactomannans according to the invention can be detected as tensing agents on the retraction model or by a panel of sensory experts.

Finally, the galactomannans of selected molecular weight do indeed exhibit a film-forming effect measured on the texturometer.

The cosmetic or dermocosmetic agent according to the invention also contains crosslinked sulfated galactans having an average molecular weight between 7 and 1100 kDa.

The sulfated galactans are known as being emulsifiers, thickeners commonly used in cosmetics and the food sector. They are polysaccharides of very large size (approximately 20,000 kDa).

The viscosity of these polysaccharides is proportional to the size of the polysaccharides and is responsible for the thickening effect.

The biopolymers of the invention thus consist of crosslinked sulfated galactans, selected preferably based on their average molecular weight between 7 and 1100 kDa, that is to say that they are preferably obtained by transformation of native sulfated galactans (of very large size), in particular by hydrolysis.

They can be obtained in particular from sulfated galactans of carrageenans (from *Kappaphycus alvarezii*, from *Kappaphycus striatum*, from *Eucheuma cottonii*, from *Eucheuma spinosum*, from *Chondrus crispus*, from *Gigartina skottsbergii*, from *Sarcothalia crispata*), or from *Fucellaria fastigiata*, from agar (*Gelidium sesquipedale*) or from algae (*Polysiphonia lanosa* or *Codium fragile*).

The particular selected sulfated galactans according to the invention, are prepared as follows:
 Solubilization of a powder of native sulfated galactans in water at a concentration of 20 g/L,
 Controlled enzymatic or chemical hydrolysis; the size of the biopolymers according to the invention is inversely proportional to the duration of the hydrolysis or to the concentration of enzyme or of chemical agent used,
 Separation of the soluble and insoluble phases, in order to eliminate the insoluble phase,
 Selection of the crosslinked sulfated galactans having an average molecular weight between 7 kDa and 1100 kDa by membrane filtration(s).

These crosslinked sulfated galactans selected based on their average molecular weight are also crosslinked by a crosslinking agent, preferably a crosslinking agent of ionic nature. The ionic crosslinking agent is selected from monovalent or multivalent cations. Other ionic crosslinking agents known to the person skilled in the art can be considered.

A liquid or low-viscosity product B is obtained, which contains crosslinked sulfated galactans having an average molecular weight between 7 kDa and 1100 kDa. These selected crosslinked sulfated galactans preferably have an average molecular weight between 8 and 200 kDa.

The characterization of the size of the crosslinked sulfated galactans is carried out by steric exclusion chromatography.

The tensing effect is evaluated on the retraction model using synthetic skin or by a panel of sensory experts.

The viscosity is determined by a viscosimeter.

The characteristic results of several examples of agents according to the invention consisting of sulfated galactans having an average molecular weight between 8 and 200 kDa, on the one hand, and of sulfated galactans having an average molecular weight outside of the range to which the invention relates are presented in Tables 2a (non-crosslinked) and 2b (crosslinked) below:

TABLE 2a

| Minimum and maximum molecular weights | Average molecular weight | Viscosity (cP) or physical state | Tensing effect on retraction model | Sensory tensing effect (g) |
|---|---|---|---|---|
| 0.18 to 8.1 kDa product FR2986430 | Between 1.08 and 3.24 kDa | liquid | – | |
| | 3.6 kDa from KA | 2.2 | – | NT** |
| 0.9 to 36.3 kDa | 5.4 kDa from KA | 15 | + | NT** |
| 1.3 to 66.1 kDa | 10.8 kDa from KA | 300 | +++ | 3.6 |
| 1.8 to 150 kDa | 14.4 kDa from KA | Liquid | +++ | |
| | 15 kDa from CC | Liquid | +++ | |
| 2.2 to 97.5 kDa | 18 kDa from KA | liquid | +++ | NT** |
| | 40 kDa from CC | Liquid | +++ | |
| | 79 kDa from CC | Liquid | +++ | NT** |
| | 185 kDa from CC | 87 | +++ | NT** |
| | 400 kDa from CC | Low viscosity | +++ | |
| | 600 kDa from CC | Low viscosity | ++ | |
| | 1100 kDa from CC | Viscous | ++ | NT** |
| Non-hydrolyzed kappa carrageenans | 1500 kDa from KA | Very viscous | – | NT** |
| | 1500 kDa from CC | Very viscous | – | NT** |

TABLE 2a-continued

| Minimum and maximum molecular weights | Average molecular weight | Viscosity (cP) or physical state | Tensing effect on retraction model | Sensory tensing effect (g) |
|---|---|---|---|---|
| Non-hydrolyzed Chondrus crispus | 3000 kDa from CC | Very viscous | – | NT** |

NM*: not measured;
NT**: not tested
KA = *Kappaphycus alvarezii*
CC = *Chondrus crispus*

These results clearly show that the native sulfated galactans of high average molecular weight (>1100 kDa) and the sulfated galactans of low average molecular weight (<7 kDa) do not exhibit the desired tensing effect.

Preferably, the crosslinked sulfated galactans having an average molecular weight between 8 and 200 kDa exhibit in fact a tensing effect visualized by a force of retraction and the desired physical state.

The selected sulfated galactans according to the invention can be detected as being tensing agents on the retraction model or by a panel of sensory experts.

TABLE 2b

| Average molecular weight | Crosslinking | Viscosity (cP) or physical aspect | Tensing effect on retraction model | Sensory tensing effect |
|---|---|---|---|---|
| <3.24 kDa | No (Product FR2986430) | Liquid | – | |
| | Yes - agent 1 | Liquid | – | |
| | Yes - agent 2 | Liquid | – | |
| | Yes - agent 3 | Liquid | – | |
| 3.6 kDa from KA | No | 2.2 | – | NT** |
| | Yes - agent 1 | liquid | – | NT** |
| | Yes - agent 2 | liquid | – | NT** |
| | Yes - agent 3 | liquid | – | NT** |
| 10.8 kDa from KA | No | 300 | +++ | 3.6 |
| | Yes - agent 1 | liquid | +++ | NT** |
| | Yes - agent 2 | liquid | +++ | NT** |
| | Yes - agent 3 | liquid | ++++ | 4.5 |
| | Yes - agent 4 | | ++++ | |
| 18 kDa from KA | No | liquid | +++ | NT** |
| | Yes - agent 3 | liquid | +++ | NT** |
| 79 kDa from CC | No | liquid | +++ | NT** |
| | Yes - agent 1 | liquid | ++++ | NT** |
| | Yes - agent 2 | liquid | +++ | NT** |
| | Yes - agent 3 | liquid | +++ | NT** |
| 3000 kDa from CC | No | 100 | – | NT** |
| | Yes - agent 1 | NM* | – | NT** |
| | Yes - agent 2 | NM* | – | NT** |
| | Yes - agent 3 | NM* | – | NT** |

NM*: not measured;
NT**: not tested
Agent 1 and 2 are ionic crosslinking agents of the bivalent cation type
Agent 3 is an ionic crosslinking agent of the monovalent cation type
Agent 4 is an ionic crosslinking agent of the multivalent cation type These results clearly show that the native sulfated galactans of high average molecular weight (>1100 kDa) and the sulfated galactans of low average molecular weight (<7 kDa) do not exhibit the desired tensing effect. The ionic crosslinking confers no tensing effect to them.

The crosslinked sulfated galactans having an average molecular weight between 7 and 1100 kDa clearly exhibit a tensing effect visualized by a retraction force.

The selected crosslinked sulfated galactans according to the invention can be detected as tensing agent on the retraction model or by a panel of sensory experts.

The ionic crosslinking of the sulfate functions potentiates the tensing effect of the selected sulfated galactans, but confers no tensing effect to sulfated galactans of excessively low or excessively high average molecular weight which have no tensing effect.

The cosmetic or dermocosmetic agent according to the invention consists of the combination of the galactomannans having an average molecular weight between 5 and 120 kDa as described above and of crosslinked sulfated galactans having an average molecular weight between 7 and 1100 kDa as described above.

The method for producing such an agent includes the following steps:
  obtention of galactomannans having an average molecular weight between 5 and 120 kDa, marked product A, according to the protocol described above,
  obtention of the crosslinked sulfated galactans having an average molecular weight between 7 and 1100 kDa, marked product B, according to the protocol described above,
  mixing of product A and product B. In particular, the cosmetic or dermocosmetic agent according to the invention can consist of:
  60 to 90% of galactomannans (product A), and
  10 to 40% of sulfated galactans (product B).

Preferably, the galactomannans and the crosslinked sulfated galactans together form an interpenetrating network.

Several agents according to the invention or outside of the invention, in the form of solutions, have been tested at 7% on the synthetic model and at 0.5% in the sensory tensing study. The results are presented in the Tables below:
  The combinations with 80% of galactomannans and 20% of crosslinked sulfated galactans in Table 3a,
  The combinations with galactomannans and crosslinked sulfated galactans having selected molecular weights according to the invention in table 3b.

TABLE 3a

| Minimum-maximum molecular weights | 20% of crosslinked sulfated galactans | 80% of galactomannans | Physical state | Tensing effect on retraction model | Tensing effect on sensory panel | Film-forming effect by texturometer (g) |
|---|---|---|---|---|---|---|
|  | <3.24 kDa from KA | 4.7 kDa from CaS | liquid | − |  |  |
|  | <3.24 kDa from KA | 19 kDa from CaS | liquid | ++ |  |  |
| 0.7 to 70 kDa | 7.2 kDa from KA | 10 kDa from CaS | liquid | ++ |  |  |
|  | 7.9 kDa from KA | 11.7 kDa from CaS | liquid | ++++ |  |  |
| 0.9 to 117 kDa | 9.4 kDa from KA | 13.3 kDa from CaS | liquid | ++++ |  |  |
|  | 12.8 kDa from KA | 20.7 kDa from CaS | liquid | ++++ |  |  |
| 1.2 to 171 kDa | 14.4 kDa from KA | 19 kDa from CaS | liquid | ++++ | 5.1 | 371 |
| 0.9 to 117 kDa | 14.8 kDa from KA | 13.5 kDa from CaS | liquid | ++++ |  |  |
| 1.5 to 190 kDa | 16.4 kDa from KA | 20.2 kDa from CaS | liquid | ++++ |  |  |
|  | 14.4 kDa from KA | 63 kDa from CyT | Liquid | ++++ | 5.0 | 466 |
|  | 20 kDa from CC | 150 kDa from CyT | viscous | +++ |  |  |
|  | 70 kDa from CC | 3 kDa from CeS | Liquid | + |  |  |
|  | 70 kDa from CC | 20 kDa from CyT | Low viscosity | +++ |  |  |
|  | 70 kDa from CC | 80 kDa from CyT | Low viscosity | ++++ |  |  |
|  | 70 kDa from CC | 150 kDa from CyT | Viscous | +++ |  |  |
|  | 79 kDa from CC | 18.9 kDa from CeS | Liquid | +++ |  |  |
|  | 220 kDa from CC | 3 kDa from CeS | viscous | + |  |  |
|  | 220 kDa from CC | 150 kDa from CyT | Very viscous | + |  |  |

NT**: not tested
KA: *Kappaphycus alvarezii*
CaS: *Caesalpinia spinoa*
CC: *Chondrus crispus*
CyT
CeS These results show that the average molecular weight of the crosslinked sulfated galactans (between 7 and 1100 kDa, preferably between 8 and 200 kDa) and the average molecular weight of the galactomannans (between 5 and 120 kDa, preferably between 8 and 80 kDa) are necessary to obtain the expected effect and physical appearance (liquid or low-viscosity).

The combination of galactomannans/crosslinked sulfated galactans in which the crosslinked sulfated galactans or the galactomannans or both have average molecular weights outside of the selection of the invention do not make it possible to obtain the expected physical state, tensing effect and film-forming effect.

One notes that the combination of selected crosslinked sulfated galactans and of selected galactomannans according to the invention not only makes it possible to preserve the tensing retraction effect of the crosslinked selected sulfated galactans or of the selected galactomannans, it also above all makes it possible to reinforce the tensing efficacy perceived by the panel of sensory experts.

TABLE 3b

| Products B selected crosslinked sulfated galactans | | Products A selected galactomannans | | Tensing effect on retraction model | Tensing effect on sensory panel | Film-forming effect by texturometer |
|---|---|---|---|---|---|---|
| Content | Average molecular weight | Content | Average molecular weight | | | |
| 10% | 14.4 kDa from KA | 90% | 19 kDa from CaS | +++ | 4.4 |  |
| 20% | 7.2 kDa from KA | 80% | 16 kDa from CaS | ++++ |  |  |
| 20% | 7.9 kDa from KA | 80% | 11.7 kDa from CaS | ++++ |  |  |
| 20% | 9.4 kDa from KA | 80% | 13.3 kDa from CaS | ++++ |  |  |
| 20% | 12.8 kDa from KA | 80% | 20.7 kDa from CaS | ++++ |  |  |
| 20% | 14.4 kDa from KA | 80% | 19 kDa from CaS | ++++ | 5.1 | 371 |
| 20% | 14.8 kDa from KA | 80% | 13.5 kDa from CaS | ++++ |  |  |
| 20% | 14.8 kDa from KA | 80% | 18 kDa from CeS | +++ |  |  |
| 20% | 14.4 kDa from KA | 80% | 80 kDa from CyT | +++ | 5.0 | 466 |
| 20% | 16.4 kDa from KA | 80% | 20.2 kDa from CaS | ++++ |  |  |
| 20% | 70 kDa from CC | 80% | 18 kDa from CeS | +++ |  |  |
| 30% | 14.4 kDa from KA | 70% | 19 kDa from CaS | +++ | 3.8 |  |
| 35% | 14.4 kDa from KA | 65% | 80 kDa from CyT | +++ |  |  |
| 50% | 14.4 kDa from KA | 50% | 19 kDa from CaS | ++ |  |  |
| 50% | 14.4 kDa from KA | 50% | 80 kDa from CyT | ++ |  |  |
| 50% | 70 kDa from CC | 50% | 18 kDa from CeS | + |  |  |

NT**: not tested

These results show the surprising effect of the interaction of the two polysaccharides of selected sizes. For example, for the 20%/80% combination, the tensing effect on the retraction model is potentiated in the combination. A similar effect is observed by the sensory panel evaluating the tensing effect.

Thus, the combinations containing between 10 and 40% of selected crosslinked sulfated galactans with between 90% and 60% of selected galactomannans exhibit the expected efficacy, a tensing and film-forming effect.

On the other hand, one notes that the 50%/50% combination of two compounds of selected sizes does not exhibit as potentiated a tensing effect on the retraction model as the other combinations according to the invention.

The combination of the selected crosslinked sulfated galactans according to the invention and of the selected galactomannans according to the invention thus makes it possible to increase the resistance of the film in comparison to the resistance of the film of the selected galactomannans according to the invention alone or of the film of the selected sulfated galactans according to the invention alone.

The cosmetic or dermocosmetic agent according to the invention can thus be used for its different properties. In particular, the invention relates to its use as a cosmetic or dermocosmetic tensing and/or film-forming agent.

Thus, it can be used, in particular:
for improving the radiance of the skin and/or for smoothening the skin, and/or
for improving the barrier effect of the skin, and/or,
for a perceptible cosmetic film effect, in order to feel the tensing efficacy, to improve the overall appearance of the face and promote the persistence of the pigments of the makeup, and/or
for a cosmetic or dermocosmetic effect protecting the skin against the penetration of toxic molecules such as pollutants, allergens, heavy metals or irritants.

Due to these different efficacies, the invention also relates to the use thereof for combating unsightly manifestations of the aging of the skin.

The invention thus also relates to:
the cosmetic use of an agent according to the invention:
as tensing and/or film-forming cosmetic agent,
as cosmetic agent for improving the radiance of the skin and/or for smoothening the skin,
as cosmetic agent for improving the barrier effect of the skin,
as cosmetic agent for combating unsightly manifestations of the aging of the skin.
the agent according to the invention, for use:
in the protection of the skin.
in the protection of the skin against the penetration of toxic molecules.

The cosmetic and/or dermocosmetic agent according to the invention is preferably used in a composition, this composition including a cosmetically acceptable medium. They are compositions in different galenic forms, suitable for administration by the topical route on the human skin.

These compositions can be present in particular in the form of oil-in-water emulsions, water-in-oil emulsions, multiple emulsions (water/oil/water or oil/water/oil) which can optionally be microemulsions or nanoemulsions, or in the form of solutions, suspensions, hydrosuspensions, aqueous gels or powders. They can be more or less fluid and have the aspect of a cream, a lotion, a milk, a serum, an ointment, a gel, a paste or a foam, or can be in solid form.

They can be compositions including at least 0.01% of an agent according to the invention, preferably between 0.05 and 1%.

These compositions include, in addition to the agent, a physiologically and preferably cosmetically acceptable medium, that is to say a medium which does not cause unacceptable sensations of discomfort for the users such as redness, tightness or tingling.

The compositions according to the invention can contain, as adjuvant, at least one compound selected from:
oils, which can be selected in particular from silicone oils, linear or cyclic, volatile or nonvolatile;
waxes, such as ozokerite, polyethylene wax, beeswax or carnauba wax,
silicone elastomers,
surfactants, preferably emulsifiers, which may be nonionic, anionic, cationic or amphoteric,
co-surfactants such as linear fatty acids,
thickeners and/or gelling agents,
moisteners such as polyols, for example, glycerol,
organic filters,
inorganic filters,
dyes, preservatives, fillers, pigments, minerals,
tensing agents,
sequestering agents,
perfumes,
and mixtures thereof, this list being non-limiting.

Examples of such adjuvants are mentioned in particular in the CTFA Dictionary (*International Cosmetic Ingredient Dictionary and Handbook published by the Personal Care Product Council*).

Naturally, the person skilled in the art will ensure that a selection is made of the optional additional, active or nonactive compounds and of the quantity thereof, in such a manner that the advantageous properties of the mixture are not altered or not substantially altered by the addition considered.

These compositions are in particular intended to be used for the effects procured by the cosmetic or dermocosmetic agent according to the invention.

The invention also specifically relates to a cosmetic method for skin care in order to improve the condition of the skin, in particular in order to improve the radiance of the skin and/or combat the unsightly manifestations of skin aging. Preferably, the method consists in applying at least once per day on the facial skin a composition including at least 0.05% by weight of dry matter of the cosmetic or dermocosmetic agent according to the invention.

In order to illustrate the invention, the following examples together with their test results are presented.

EXAMPLES

Example 1: Selected Galactomannans Obtained from *Caesalpinia spinosa*

An example of an agent according to the invention is an agent consisting of galactomannans having an average molecular weight of 10 kDa, obtained from *Caesalpinia spinosa*.

This agent can be obtained by the use of a method including the following steps:
Solubilization of a powder of native galactomannans from *Caesalpinia spinosa* in water at 20 g/L,
Controlled acid hydrolysis for 2 h,
Settling in order to separate the soluble phase and the insoluble phase, and to eliminate the insoluble phase, Membrane filtration in order to select the polysaccharides having an average molecular weight of 10 kDa.

The agent obtained is characterized by an average molecular weight of 10 kDa.

Example 2: Selected Galactomannans Obtained from *Ceratonia siliqua*

An example of an agent according to the invention is an agent consisting of galactomannans having an average molecular weight of 18.9 kDa obtained from *Ceratonia siliqua*.

This agent can be obtained by carrying out a method including the following steps:
Solubilization of a powder of native galactomannans from *Ceratonia siliqua* in water at 20 g/L,
Controlled acid hydrolysis for 1 h,
Settling in order to separate the soluble phase and the insoluble phase, and to eliminate the insoluble phase,
Membrane filtration in order to select the polysaccharides having an average molecular weight of 18.9 kDa.

The agent obtained is characterized by an average molecular weight of 18.9 kDa.

Example 3: Selected Galactomannans Obtained from *Cyamopsis tetragonoloba*

An example of an agent according to the invention is an agent consisting of galactomannans having an average molecular weight of 63 kDa, obtained from *Cyamopsis tetragonoloba*.

This agent can be obtained by carrying out a method including the following steps:
Solubilization of a powder of native galactomannans from *Cyamopsis tetragonoloba* in water at 20 g/L,
Enzymatic hydrolysis for 30 min,
Settling in order to separate the soluble phase and the insoluble phase and to eliminate the insoluble phase,
Membrane filtration in order to select the polysaccharides having an average molecular weight of 63 kDa.

The agent obtained is characterized by an average molecular weight of 63 kDa.

Example 4: Non-Crosslinked Selected Sulfated Galactans Obtained from *Kappaphycus alvarezii*

An example of an agent according to the invention is an agent consisting of non-crosslinked sulfated galactans having an average molecular weight of 10.8 kDa, obtained from *Kappaphycus alvarezii*.

This agent can be obtained by carrying out a method including the following steps:
Solubilization of a powder of native sulfated galactans from *Kappaphycus alvarezii* in water at 20 g/L,
Controlled acid hydrolysis for 3 h,
Filtration in order to separate the soluble phase and the insoluble phase, and to eliminate the insoluble phase,
Membrane filtration and selection of the polysaccharides having an average molecular weight of 10.8 kDa.

The agent obtained is characterized by an average molecular weight of 10.8 kDa.

Example 5: Crosslinked Selected Sulfated Galactans Obtained from *Kappaphycus alvarezii*

An example of an agent according to the invention is an agent consisting of crosslinked sulfated galactans having an average molecular weight of 10.8 kDa, obtained from *Kappaphycus alvarezii*.

This agent can be obtained by carrying out a method including the following steps:
Method of example 4
Addition of the crosslinking agent, CaCl2,
Filtration in order to separate the soluble phase and the insoluble phase, and to eliminate any insoluble fraction.

The agent obtained is characterized by an average molecular weight of 10.8 kDa.

Example 6: Non-Crosslinked Sulfated Galactans Obtained from *Chondrus Crispus*

An example of an agent according to the invention is an agent consisting of non-crosslinked sulfated galactans having an average molecular weight of 79 kDa, obtained from *Chondrus crispus*.

This agent can be obtained by carrying out a method including the following steps:
Solubilization of a powder of native sulfated galactans from *Chondrus crispus* in water at 20 g/L,
Controlled enzymatic hydrolysis for 1 h,
Settling in order to separate the soluble phase and the insoluble phase, and to eliminate the insoluble phase,
Membrane filtration in order to select the polysaccharides having an average molecular weight of 79 kDa.

The agent obtained is characterized by an average molecular weight of 79 kDa.

Example 7: Crosslinked Selected Sulfated Galactans Obtained from *Chondrus crispus*

An example of an agent according to the invention is an agent consisting of crosslinked sulfated galactans having an average molecular weight of 79 kDa, obtained from *Chondrus crispus*.

This agent can be obtained by carrying out a method including the following steps:
Method of example 6
Addition of the crosslinking agent, CaCl2,
Filtration in order to separate the soluble phases and the insoluble phases, and to eliminate any insoluble fraction.

The agent obtained is characterized by an average molecular weight of 79 kDa.

Example 8: Combination of Galactomannans According to the Invention Obtained from Tara and of Crosslinked Sulfated Galactans According to the Invention Obtained from *Kappaphycus alvarezii*

An example of an agent according to the invention is an agent consisting of a mixture of galactomannans according to the invention obtained from tara having an average molecular weight of 10 kDa and of crosslinked sulfated galactans according to the invention having an average molecular weight of 10.8 kDa obtained from *Kappaphycus alvarezi*.

This agent can be obtained by carrying out a method including the following steps:
Carrying out the methods of examples 1 and 5,
Mixing 90% of example 1 and 10% of example 5, Example 10: Combination According to the Invention of Galactomannans Obtained from *Cyamopsis tetragonoloba* and of Crosslinked Sulfated Galactans According to the Invention Obtained from *Kappaphycus alvarezi*

An example of an agent according to the invention is an agent consisting of a mixture of galactomannans according to the invention obtained from *Cyamopsis tetragonoloba* having an average molecular weight of 63 kDa and of crosslinked sulfated galactans according to the invention having an average molecular weight of 10.8 kDa obtained from *Kappaphycus alvarezi*.

This agent can be obtained by carrying out a method including the following steps:
Carrying out the methods of examples 3 and 5,
Mixing 65% of example 3 and 35% of example 5,
Membrane filtration in order to eliminate the insoluble compounds.

Example 10: Combination According to the Invention of Galactomannans Obtained from Carob and of Crosslinked Sulfated Galactans According to the Invention Obtained from *Chondrus Crispus*

An example of an agent according to the invention is an agent consisting of a mixture of galactomannans according to the invention obtained from carob having an average molecular weight of 18.9 kDa and of crosslinked sulfated galactans according to the invention having an average molecular weight of 79 kDa obtained from *Chondrus crispus*.

This agent can be obtained by carrying out a method including the following steps:
Carrying of the methods of examples 2 and 7,
Mixing 80% of example 2 and 20% of example 7,
Membrane filtration in order to eliminate the insoluble compounds.

All these examples of agents exhibit film-forming and tensing effects (see results of Tables 1 to 3).

These examples are not limiting, and the results of tests with other examples (which are also not limiting) have also been presented in the preceding tables.

The invention claimed is:

1. A cosmetic or dermocosmetic agent, said cosmetic or dermocosmetic agent being film-forming on the surface of the skin and having a tensing effect when solubilized with water, the cosmetic or dermocosmetic agent consisting of:
hydrolyzed, soluble galactomannans having a low viscosity of less than 1000 centipoise when solubilized with water and average molecular weights between 5 and 120 kDa in an amount from 65 to 90% by weight,
hydrolyzed, soluble crosslinked sulfated galactans having a low viscosity of less than 1000 centipoise when solubilized with water and average molecular weights between 7 and 1100 kDa in an amount from 10 to 35% by weight.

2. The cosmetic or dermocosmetic agent according to claim 1, characterized in that the galactomannans are obtained by hydrolysis of native galactomannans from *Caesalpinia spinosa*, from *Cyamopsis tetragonoloba*, from *Ceratonia siliqua*, from *Cassia angustifolia*, from *Cassia fistula*, from *Cassia obtusifolia* or *Cassia tora*, from *Gleditsia sinensis*, from *Gleditsia triacanthos*, from *Sophora japonica* and/or from *Trigonella foenum-graecum*.

3. The cosmetic or dermocosmetic agent according to claim 1, characterized in that the galactomannans have an average molecular weight between 8 and 80 kDa.

4. The cosmetic or dermocosmetic agent according to claim 1, characterized in that the crosslinked sulfated galactans are obtained by hydrolysis of native sulfated galactans from *Kappaphycus alvarezii*, from *Eucheuma cottonii*, from *Chondrus crispus*, from *Gigartina skottsbergii*, from *Sarcothalia crispata*, from *Kappaphycus striatum*, from *Eucheuma spinosum*, from *Fucellaria fastigiata*, from *Gelidium sesquipedale*, from *Polysiphonia lanosa* and/or from *Codium fragile*.

5. The cosmetic or dermocosmetic agent according to claim 1, characterized in that the crosslinked sulfated galactans have an average molecular weight between 8 and 200 kDa.

6. The cosmetic or dermocosmetic agent according to claim 1, characterized in that the sulfated galactans are crosslinked with a crosslinking agent of ionic nature.

7. The agent according to claim 1, wherein the agent has a function of protecting skin.

8. The agent according to claim 1, wherein the agent protects skin against penetration of toxic molecules.

9. The agent according to claim 1, wherein the agent combats unsightly manifestations of skin aging.

10. A cosmetic composition suitable for topical application on the human skin, the cosmetic composition comprising at least 0.01% of a cosmetic or dermocosmetic agent according to claim 1.

11. A cosmetic method for improving skin, characterized in that it consists in applying the cosmetic composition according to claim 10 on the skin.

12. The cosmetic method according to claim 11, wherein the application improves the radiance of the skin.

13. The cosmetic method according to claim 11, wherein the application combats unsightly manifestations of skin aging.

14. A cosmetic method, the method comprising applying the composition of claim 10 on skin, and thereby tensing the skin and/or forming a film on the skin.

15. A cosmetic method, the method comprising applying the composition of claim 10 on skin, and thereby improving the radiance of the skin and/or smoothening the skin.

16. A cosmetic method, the method comprising applying the composition of claim 10 on skin, and thereby improving a barrier effect of the skin.

* * * * *